United States Patent [19]

De Wald

[11] 4,260,623

[45] Apr. 7, 1981

[54] HEXAHYDRO-1-ARYLSPIRO(3H-OXAZOLO(3,4-a)PYRIDINE-3,4'-PIPERIDENE) ANTIDEPRESSANTS, PHARMACEUTICAL COMPOSITIONS THEREOF AND METHOD OF USE THEREOF

[75] Inventor: Horace A. De Wald, Ann Arbor, Mich.

[73] Assignee: Warner-Lambert Company, Morris Plains, N.J.

[21] Appl. No.: 97,571

[22] Filed: Nov. 26, 1979

[51] Int. Cl.³ .................. C07D 498/20; A61K 31/445
[52] U.S. Cl. ..................................... 424/267; 546/17; 546/19; 546/241; 546/242; 546/216
[58] Field of Search ..................... 546/19, 17; 424/267

[56] References Cited

U.S. PATENT DOCUMENTS

| | | | |
|---|---|---|---|
| 3,840,547 | 10/1974 | Mendelson | 546/314 |
| 3,957,828 | 5/1976 | Bauer et al. | 424/283 |
| 3,959,475 | 5/1976 | Bauer et al. | 546/17 |

OTHER PUBLICATIONS

Marxer et al., "J. Org. Chem.", vol. 40, No. 10, pp. 1427-1433, (1975).
Bauer et al., "J. Med. Chem.", vol. 19, No. 11, pp. 1315-1324, (1976).
Klioze et al., "J. Med. Chem.", vol. 20, No. 4, pp. 610-612, (1977).
Parham et al., "J. Org. Chem.", vol. 41, No. 15, pp. 2628-2633, (1976).
Salama et al., "Arch. Int. Pharmacodyn", vol. 225, pp. 317-329, (1977).
Crook et al., "J. Am. Chem. Soc.", vol. 52, pp. 4006-4011, (1930).
Novel Tetracycic Spiropiperidines and Related Compounds as Potential Psychotropic Agents, L. L. Martin et al., Am. Chem. Soc., Div. of Med. Chem., 178th National Meeting, Sep. 10 to 13, 1979, Washington, D.C.
Arya et al., "Indian J. Chem.", Section B (1976), vol. 14B, No. 10, pp. 777-779.
Morrison and Boyd, "Organic Chemistry", 3rd Ed. (Allyn and Bacon), (1973), pp. 745-748.

Primary Examiner—Robert T. Bond
Attorney, Agent, or Firm—Walter Patton

[57] ABSTRACT

Compounds of the formula

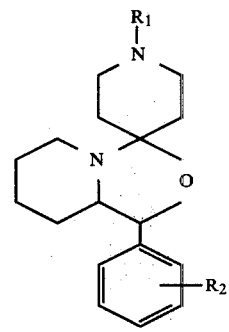

where $R_1$ is hydrogen, lower alkyl containing one to three carbon atoms, cycloalkyl lower alkyl containing four to seven carbon atoms, or benzyl; and $R_2$ is hydrogen, halogen, alkoxy containing one to three carbon atoms, trifluoromethyl; and pharmaceutically acceptable acid addition salts thereof are useful as anti-depressants.

11 Claims, No Drawings

HEXAHYDRO-1-ARYLSPIRO(3H-OXAZOLO(3,4-A)PYRIDINE-3,4'-PIPERIDENE) ANTIDEPRESSANTS, PHARMACEUTICAL COMPOSITIONS THEREOF AND METHOD OF USE THEREOF

BACKGROUND OF THE INVENTION

This invention relates to hexahydro-1-arylspiro[3H-oxazolo-[3,4-a]pyridine-3,4'-piperidine] compounds and acid addition salts thereof which can be used to treat depression. U.S. Pat. No. 3,959,475 to V. J. Bauer and R. W. Kosley, issued May 25, 1976, described 1,3-dihydrospiro(isobenzofurans) which have anti-depressant activity. U.S. Pat. No. 3,957,828 to V. J. Bauer and H. H. Ong, issued May 18, 1976, discloses 3-aminoalkyl-1,3-dihydro-3-phenylspiro(isobenzofurans) which possess tranquilizing properties. The synthesis of spirocyclic oxazolo[3,4-a]pyridines and pyrido [1,2-c]-[1,3]oxazines is described by V. P. Arya, et al., in the Indian J. of Chem. 14B, 777–779 (1976). The synthesis of spiro[isobenzofuran-1(3H),4'-piperidines] and spiro[isobenzofuran-1(3H)-3'-piperidines] is described by A. Marxer, et al., in the J. Org. Chem. 40. 1427–1433 (1975). The synthesis of spiro[isobenzofuran-1(3H),4'-piperidines] as potential central nervous system agents is also described by V. J. Bauer, et al., in J. Med. Chem. 19, 1315–1324 (1976). The synthesis of spiro[isobenzofuran-1(3H),4'-piperidine]-3-ones, spiro[isobenzofuran-1(3H),4'-piperidines] and spiro[isobenzotetrahydrothiophene-1(3H)-4'-piperidines] is described by W. E. Parham, et al., in the J. Org. Chem. 41, 2628–2633 (1976).

SUMMARY

This invention relates to hexahydro-1-arylspiro[3H-oxazolo[3,4-a]pyridine-3,4'-pyridine] compounds having the formula

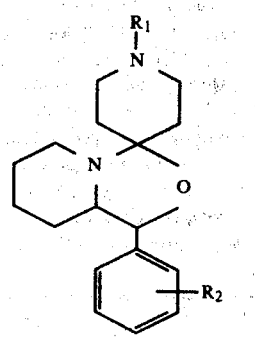

where $R_1$ is hydrogen, lower alkyl containing one to three carbon atoms, cycloalkyl lower alkyl containing four to seven carbon atoms, or benzyl; and $R_2$ is hydrogen, halogen, alkoxy containing one to three carbon atoms, or trifluoromethyl; and to pharmaceutically acceptable acid addition salts thereof.

The invention also relates to methods for producing said compounds and their pharmaceutically acceptable acid addition salts. Additionally, the invention relates to pharmaceutical compositions for treating depression in mammals which comprise an effective amount of one of the aforesaid compounds and/or a pharmaceutically acceptable acid addition salt thereof together with an inert pharmaceutical carrier. "Effective amount" means an amount sufficient to bring about the desired antidepressant effect. Additionally, the invention relates to a method of treating depression in mammals by administering an effective amount of one of the aforesaid compounds or a pharmaceutically acceptable acid addition salt thereof.

The hexahydro-1-arylspiro[3H-oxazolo[3,4-a]pyridine-3,4'-piperidine] compounds of the invention can be prepared by reacting an alpha-aryl-2-piperidinemethanol compound of the formula

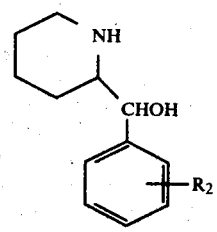

with a 4-piperidone compound of formula,

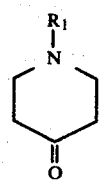

where $R_1$ and $R_2$ are as defined above.

The reaction is preferably carried out in a solvent medium of an aromatic hydrocarbon, such as xylene, toluene, chlorobenzene, and mixtures thereof. The temperature and duration of the reaction may be varied over a wide range, the temperature from about 75° C. to about 200° C. and the duration from about 2 to about 72 hours. The reaction is most conveniently carried out at or above the boiling point of the reaction mixture, in the presence of an organic sulfonic acid as a catalyst. At such temperature, the reaction is essentially complete after a period of from about six to about 24 hours. To expedite the completion of the reaction it is preferable to remove the water as it is formed. This may be done in a number of ways, for example, by the use of a mechanical device such as a Dean-Stark water separator. While an excess of either reagent may be employed, equivalent quantities are usually preferred. The reaction product may be isolated either in free base form or in the form of an acid-addition salt utilizing conventional procedures such as extraction, acidification, basification, chromatography, and crystallization.

The compounds of the invention can also be produced by a variety of other methods.

The compounds where $R_1$ is hydrogen and $R_2$ is as defined above can be produced by hydrogenation of the corresponding hexahydro-1-aryl-1'-benzylspiro[3H-oxozolo[3,4-a]pyridine-3,4'-piperidine] or the acid addition salt thereof. The hydrogenation is carried out using gaseous hydrogen and a hydrogenation catalyst such as palladium on carbon, Raney nickel, or platinum oxide. The reaction is preferably carried out in a solvent such as a lower alkanol, a lower alkanoic acid, or a mixture thereof. The hydrogenation is usually carried out using hydrogen pressures of about one to fifteen atmospheres at a temperature of about 20° C. to 75° C.

The compounds of the invention wherein $R_1$ is lower alkyl, cycloalkyl lower alkyl or benzyl and $R_2$ is as defined above can be produced by alkylation of the corresponding hexahydro-1-arylspiro[3H-oxazolo[3,4-a]pyridine-3,4'-piperidine] wherein $R_1$ is hydrogen and $R_2$ is as defined above. The alkylation may be carried out by reacting the aforesaid hexahydro-1-arylspiro[3H-oxazolo[3,4-a]-pyridine-3,4'-piperidine] with a $R_1$ halide, di-$R_1$ sulfate, or $R_1$-phenyl sulfonate (where $R_1$ is lower alkyl, cycloalkyl lower alkyl, or benzyl). The reaction is usually carried in a solvent and preferably in the presence of a base. As a solvent tertiary amides such as dimethylformamide and 1-methyl-2-pyrrolidinone; aromatic hydrocarbons such as benzene, toluene and xylene; lower alkane ketones such as acetone and methyl ethyl ketone; and ethers such as diethyl ether, tetrahydrofuran, and dioxane; and tertiary amines such as pyridine, alpha-picoline, and triethylamine may be used. Some examples of the bases which can be used for the reaction are sodium alkoxide, sodium hydride, sodium amides, butyl lithium and potassium carbonate. When the reaction is carried out in a tertiary amine as a solvent, the solvent also serves as a base. The temperature and duration of the reaction may be varied over a wide range; the temperature from about $-5°$ C. to $125°$ C. and the duration from about 2 to 36 hours. Best results are obtained by using from 1.1 to 2 equivalents of the alkylating agent and about 1.1 equivalents of the base for each equivalent of the hexahydro-1-arylspiro[3H-oxazolo[3,4-a]pyridine-3,4'-piperidine] compound.

The compounds of the invention wherein $R_1$ is a lower alkyl or a cycloalkyl lower alkyl group and $R_2$ is as defined above can also be produced from the corresponding hexahydro-1-arylspiro[3H-oxazolo[3,4-a]pyridine-3,4'-piperidines] wherein $R_1$ is hydrogen and $R_2$ is as defined above by a two step alkylation process wherein the hexahydro-1-arylspiro[3H-oxazolo[3,4-a]pyridine-3,4'-piperidine] compound is first acylated with a derivative of an alkanoic or cycloalkanoic acid and the resulting 1'-alkanoyl or cycloalkanoyl derivative or acid addition salt thereof then reduced. The first step of this process is carried out by reacting the hexahydro-1-arylspiro[3H-oxazolo[3,4-a]pyridine-3,4'-piperidine] compound with an alkanoic or cycloalkanoic acid halide or anhydride in an inert solvent such as methylene dichloride, dichloromethane, chloroform, benzene, toluene, ether, tetrahydrofuran or dioxane, preferably in the presence of an acid acceptor such as triethylamine or pyridine. The second or reduction step of the process is carried out using an inorganic hydride reducing agent such as lithium aluminum hydride or sodium borohydride. This step is usually carried out in an inert solvent such as ether, tetrahydrofuran or a mixture thereof at a temperature between about $-10°$ C. and $60°$ C. The time of the reaction is not critical and can be varied from about 0.5 to 25 hours. Although equivalent amounts of the reactants can be used, it is preferable to use an excess of the reducing agent.

The various starting materials for producing the hexahydro-1-arylspiro[3H-oxazolo[3,4-a]pyridine-3,4'-piperidine] compounds of the invention are known or are readily available by known procedures. For example, alpha-aryl-2-piperidinemethanols are described by K. Crook, et al., in J. Amer. Chem. Soc., 52, 4006 (1930).

The compounds of the present invention may exist in the free base form, or in the form of an acid-addition salt. Pharmaceutically acceptable acid addition salts are formed by the reaction of the free base with any number of inorganic or organic acids, including hydrochloric, hydrobromic, hydroiodic, sulfuric, nitric, phosphoric, acetic, benzoic, citric, maleic, malic, tartaric, succinic, gluconic, ascorbic, sulfamic, pamoic, methanesulfonic and benzenesulfonic acid. The free base compounds and their salts may differ slightly in certain physical properties, such as solubility in polar solvents, but they are otherwise equivalent for purposes of the present invention. The compounds of the present invention may exist in anhydrous form, as well as in solvated or hydrated forms. In general, the hydrated forms and the solvated forms with pharmaceutically acceptable solvents are equivalent to the anhydrous or unsolvated forms of the present invention. The compounds of the present invention may also exist in the forms of their optical antipodes and their pharmaceutically acceptable salts of these optical antipodes. The compounds of the present invention may also exist in the form of cis and trans isomers with respect to the spacerelationship of the 1-aryl substitutent to the oxazolo[3,4-a]pyridine system and their pharmaceutically acceptable salts.

As pharmacological agents, the compounds of the present invention exhibit anti-depressant activity which can be demonstrated and quantitatively determined in a pharmacological assay which measures the ability of a test compound to inhibit the neuronal-uptake of norepinephine and/or serotonin [A. I. Salama and M. E. Goldberg, Arch. Int. Pharmacoldyn 225, 317–329 (1977)].

According to this procedure, male mice weighing approximately 25 grams are fasted overnight, then groups of five or more mice are dosed with the test compound or methocel vehicle at 50 mg/kg by oral route. After an interval of one hour, the mice are given an intravenous injection of a saline solution containing 0.5 $\mu$Ci of norepinephrine-$^3$H, 0.5 $\mu$Ci of serotonin$^{14}$C, and 1 mg/ml of ascorbic acid. The mice are then sacrificed about 15 minutes later, their hearts and spleens rinsed and weighed, and dissolved in a tissue solubilizer. The tritium content of the hearts and carbon-14 content of the spleen are determined by scintillation counting. The percent inhibition of uptake in comparison with the vehicle control group is then recorded.

The results obtained in this assay for representative compounds of this invention are shown in the following table, where the compounds are identified by name and by reference to the examples that follow.

| | % Inhibition of Amine Uptake at 50 mg/kg. | |
|---|---|---|
| | Norepinephrine | Serotonin |
| Example 2 Hexahydro-1-phenylspiro[3H-oxazolo[3,4-a]pyridine-3,4'-piperidine] | 70 | 83 |
| Example 3 Hexahydro-1'-methyl-1-phenylspiro[3H-oxazolo[3,4-a]pyridine-3,4'-piperidine] | 73 | 73 |
| Example 4 Hexahydro-1'-benzyl-1-(3-fluorophenyl)spiro[3H-oxazolo[3,4-a]pyridine-3,4'-piperidine] | 58 | 79 |
| Example 5 Hexahydro-1-(3-fluorophenyl)spiro[3H-oxazolo[3,4-a]pyridine-3,4'-piperidine] | 70 | 89 |
| Example 7 Hexahydro-1-(2-methoxyphenyl)spiro[3H-oxazolo[3,4-a]pyridine-3,4'-piperidine] | 67 | 71 |
| Example 9 Hexahydro-1-[3-(trifluoro- | | |

-continued

| | % Inhibition of Amine Uptake at 50 mg/kg. | |
|---|---|---|
| | Norepinephrine | Serotonin |
| methyl)phenyl]spiro[3H-oxazolo[3,4-a]-pyridine-3,4'-piperdine] | 64 | 86 |
| Example 11 Hexahydro-1-(4-fluorophenyl)-spiro[3H-oxazolo[3,4-a]pyridine-3,4'-piperdine] | 73 | 89 |
| Example 12 Hexahydro-1'-benzyl-1-(4-chlorophenyl)spiro[3H-oxazolo[3,4-a]-pyridine-3,4'-piperidine] | 59 | 84 |
| Example 13 Hexahydro-1'-methyl-1-(4-chlorophenyl)spiro[3H-oxazolo[3,4-a]-pyridine-3,4'-piperidine] | 77 | 91 |
| Example 14 Hexahydro-1-(4-methoxyphenyl)-spiro[3H-oxazolo[3,4-a]pyridine-3,4'-piperidine] | 57 | 89 |
| Example 15 Hexahydro-1'-(cyclopropylmethyl)-1-phenylspiro[3H-oxazolo[3,4-a]-pyridine-3,4'-piperidine] | 62 | 77 |

The compounds of the invention, and/or the pharmaceutically acceptable salts thereof, may be administered to mammals in pharmaceutical formulations comprising the compounds of the invention together with a pharmaceutically acceptable carrier. The compounds of the invention may be administered parenterally in combination with conventional injectable liquid carriers such as sterile pyrogen-free water, sterile peroxide-free ethyl oleate, dehydrated alcohols, propylene glycol, and mixtures thereof. Suitable pharmaceutical adjuvants for the injecting solutions includes stabilizing agents, solubilizing agents, buffers and viscosity regulators. Some examples of these adjuvants are ethanol, ethylenediamine tetra-acetic acid, tartrate buffers, citrate buffers, and high molecular weight polyethylene oxides. These pharmaceutical formulations may be injected intramuscularly, intraperitoneally, or intravenously.

The compounds of the invention, and/or the pharmaceutically acceptable salts thereof, may be administered to mammals orally in combination with conventionally compatible carriers in solid or in liquid form. These oral compositions may contain binding agents such as syrups, acacia, gelatin, sorbitol, tragacanth, polyvinylpyrrolidone, and mixtures thereof; fillers such as lactose, mannitols, starch, calcium phosphate, sorbitol, methylcellulose, and mixtures thereof; lubricants such as magnesium stearate, high-molecular weight polymers such as polyethylene glycol, high-molecular weight fatty acids such as stearic acid or silica; disintegrants such as starch; and wetting agents such as sodium lauryl sulfate.

The oral compositions may take any convenient form such as tablets, capsules, lozenges, aqueous or oily suspensions, emulsions, or dry powders which may be reconstituted with water or other liquid medium before use. The solid or liquid oral forms may contain flavors, sweeteners, preservatives such as alkyl p-hydroxybenzoates. The liquid forms may contain suspending agents such as sorbitol, glucose or other sugar syrups, methyl, hydroxymethyl, or carboxymethyl cellulose, and gelatin; emulsifying agents such as lecithin or sorbitan monooleate; and conventional thickening agents. The liquid composition may optionally be encapsulated in capsules, for example gelatin capsules.

The dosage levels of the compounds of the present invention will depend on the nature or severity of the depression, as well as on the route of administration. The compounds of the present invention may be administered in dosages from about 1.0 to about 300 mg/kg. A more typical dosage is from about 2 to about 250 mg/kg while the most typical dose is from about 10 to about 200 mg/kg. The age, weight, and health of the patient will have to be taken into account when determining optimal dosage levels to be administered.

The invention is illustrated by the following Examples.

EXAMPLE 1

Hexahydro-1'-benzyl-1-phenylspiro[3H-oxazolo[3,4-a]pyridine-3,4'-piperidine]

A mixture of 19 g of alpha-phenyl-2-piperidinemethanol, 20 g of N-benzyl-4-piperidone, and 0.3 g of p-toluenesulfonic acid in 160 ml of xylene is stirred and heated under reflux for 48 hours in a vessel provided with a Dean-Stark water separator. The reaction mixture is decanted from some gum and allowed to stand overnight whereupon the first crop of product separates as crystals which are collected by filtration. The filtrate is evaporated in vacuo and the residue dissolved in 40 ml of hot ethyl acetate and refrigerated to obtain a second crop of crystalline product. Recrystallization of the combined crops of crystals from methanol gives 19.5 g colorless crystals of hexahydro-1'-benzyl-1-phenylspiro[3H-oxazolo[3,4-a]-pyridine-3,4'-piperidine]; mp 148°–151° C.

EXAMPLE 2

Hexahydro-1-phenylspiro[3H-oxazolo[3,4-a]pyridine-3,4'-piperidine]

A solution of 11 g of hexahydro-1'-benzyl-1-phenylspiro[3H-oxazolo[3,4-a]pyridine-3,4'-piperidine] in 95 ml of methanol and 5 ml of acetic acid is mixed with 1 g of 20% palladium on carbon and subjected to hydrogen pressure of about 50 p.s.i. After the theoretical amount of hydrogen is consumed, the reaction is stopped and the filtered solution is evaporated to dryness in vacuo. The residue is dissolved in methylene dichloride and stirred with excess dilute ammonium hydroxide solution to convert the acetate salt of hexahydro-1-phenylspiro[3H-oxazolo[3,4-a]pyridine-3,4'-piperidine] to the free base. The organic layer containing the aforementioned free base is separated, washed with a saturated sodium bicarbonate solution, dried over magnesium sulfate and evaporated to dryness in vacuo. The residue is recrystallized from ethyl acetate or methanol-water to obtain the pure free base of hexahydro-1-phenylspiro[3H-oxazolo[3,4-a]pyridine-3,4'-piperidine]; mp 169°–171° C.; yield 7 g.

EXAMPLE 3

Hexahydro-1'-methyl-1-phenylspiro[3H-oxazolo[3,4-a]pyridine-3,4'-piperidine]

Sodium hydride (1.2 g of a 50% dispersion in a mineral oil) is added in portions to a stirred solution of 5.4 g of hexahydro-1-phenylspiro[3H-oxazolo[3,4-a]pyridine-3,4'-piperidine] in 100 ml of tetrahydrofuran at 25° C. The mixture is stirred 0.5 hours under nitrogen and 5 g iodomethane in 10 ml of tetrahydrofuran is added dropwise. The mixture is stirred at 45° C. for 3 hours, filtered and the filtrate is evaporated in vacuo. The residue is dissolved in methylene dichloride, washed with water, dried over magnesium sulfate and the solvent is evaporated. The residue is crystallized from ethyl acetate to obtain the desired hexahydro-1'-methyl-1-phenylspiro[3H-oxazolo-[3,4-a]pyridine-3,4'-piperidine]; mp 157°–159° C.

EXAMPLE 4

Hexahydro-1'-benzyl-1-(3-fluorophenyl)spiro[3H-oxazolo[3,4-a]pyridine-3,4'-piperidine]

Utilizing the procedure described in Example 1 above, 11 g of alpha-(3-fluorophenyl)-2-piperidinemethanol is reacted with 10 g of N-benzyl-4-piperidone to obtain hexahydro-1'-benzyl-1-(3-fluorophenyl)-spiro[3H-oxazolo[3,4-a]pyridine-3,4'-piperidine]; mp 113°–115° C. after recrystallizaton from petroleum ether.

If desired, the hexahydro-1'-benzyl-1-(3-fluorophenyl)spiro[3H-oxazolo-[3,4-a]pyridine-3,4'-piperidine] may be isolated as the hydrochloride salt by treating the dried methylene dichloride solution of the free base with anhydrous hydrogen chloride and collecting the insoluble hydrochloride salt which separates from the solution.

The alpha-(3-fluorophenyl)-2-piperidinemethanol used as a starting material in the above procedure can be prepared as follows.

A solution of 17.4 g of 2-bromopyridine in 40 ml of ether is added slowly with stirring to 75 ml of commercial n-butyl lithium in heptane and 100 ml of ether at −50° to −40° C. under a nitrogen atmosphere. After stirring another 0.25 hours at −40° C., a solution of 12.5 g of 3-fluorobenzaldehyde in 30 ml of ether is added dropwise and the mixture is allowed to warm to room temperature. After stirring 3 hours, 100 ml of water is added, the organic layer is separated, dried over MgSO$_4$ and the solvent is evaporated. The residue is chromatographed over silica gel in acetonitrile to obtain alpha-(3-fluorophenyl)-2-pyridinemethanol; mp 80°–82° C., after recrystallization from cyclohexane. The alpha-(3-fluorophenyl)-2-pyridinemethanol is hydrogenated at about 50 lbs. p.s.i. in methanol-acetic acid in the presence of 10% Rh/C. The reaction mixture is filtered, the solvent evaporated from the filtrate, and the residue dissolved in methylene dichloride and shaken with concentrated sodium hydroxide. The organic layer is separated, dried, and concentrated to obtain the desired alpha-(3-fluorophenyl)-2-piperidinemethanol; mp 146°–148° C.

EXAMPLE 5

Hexahydro-1-(3-fluorophenyl)spiro[3H-oxazolo-[3,4-a]pyridine-3,4'-piperidine]

Utilizing the procedure described in Example 2 above, 7.6 g hexahydro-1'-benzyl-1-(3-fluorophenyl)-spiro[3H-oxazolo[3,4-a]pyridine-3,4'-piperidine] is hydrogenated to yield hexahydro-1-(3-fluorophenyl)-spiro[3H-oxazolo[3,4-a]pyridine-3,4'-piperidine]; mp 133°–135° C., after recrystallization from ethyl acetate-petroleum ether.

EXAMPLE 6

Hexahydro-1'-benzyl-1-(2-methoxyphenyl)spiro[3H-oxazolo[3,4-a]pyridine-3,4'-piperidine] Oxalate Salt Utilizing the procedure described in Example 1 above, 12 g of alpha-(2-methoxyphenyl)-2-piperidinemethanol is reacted with 10 g of N-benzyl-4-piperidone. Evaporation of the filtrate in vacuo yields the desired hexahydro-1'-benzyl-1-(2-methoxyphenyl)-spiro[3H-oxazolo[3,4-a]pyridine-3,4'-piperidine] as an oil. The oil, 3.5 g, is dissolved in 10 ml ether and added to a solution of 1.25 g oxalic acid dihydrate in 20 ml of ether. The precipitated solid is collected by filtration and recrystallized from methanol-ethyl acetate to obtain the 1.5 oxalate salt; mp 124°–126° C.

The alpha-(2-methoxyphenyl)-2-piperidinemethanol used as a starting material in the above procedure can be prepared as follows: 2-Pyridyl lithium is reacted with 2-methoxybenzaldehyde in ether. Water is added to the reaction mixture, and the organic layer separated and dried. After evaporation of the ether and purification by chromatography over silica gel in acetonitrile, the alpha-(2-methoxyphenyl)-2-pyridinemethanol is hydrogenated in methanol-acetic acid in the presence of 10% Rh/C catalyst to obtain the desired alpha-(2-methoxyphenyl)-2-piperidinemethanol; mp of the hydrochloride salt 222°–224° C.

EXAMPLE 7

Hexahydro-1-(2-methoxyphenyl)spiro[3H-oxazolo[3,4-a]pyridine-3,4'-piperidine] Oxalate Salt Utilizing the procedure described in Example 2 above, 8.9 g of hexahydro-1'-benzyl-1-(2-methoxyphenyl)spiro[3H-oxazolo[3,4-a]pyridine-3,4'-piperidine] is hydrogenated in the presence of a palladium on charcoal catalyst to obtain hexahydro-1-(2-methoxyphenyl)-spiro[3H-oxazolo[3,4-a]pyridine-3,4'-piperidine] as an oil after evaporation of the organic layer. The oil, 5.8 g, is dissolved in 30 ml ether and added to a solution of 2.4 g oxalic acid dihydrate in 40 ml of ether. The precipitated solid is collected by filtration and recrystallized from methanol-ethyl acetate to obtain the oxalate salt; mp 185°–186° C.

EXAMPLE 8

Hexahydro-1'-benzyl-1-[3-(trifluoromethyl)phenyl]-spiro[3,4-oxazolo[3,4-a]pyridine-3,4'-piperidine] Oxalate Salt A mixture of 8.9 g alpha-(3-trifluoromethylphenyl)-2-piperidinemethanol, 7 g of N-benzyl-4-piperidone, and 0.2 g of p-toluenesulfonic acid in 150 ml of xylene is stirred under reflux for 48 hours in a vessel provided with a Dean-Stark water separator. The cooled mixture is filtered and evaporated in vacuo. The residue is applied to a silica gel column in ethyl acetate and chromatographed. The partially purified free base product (7 g) is dissolved in 75 ml of ether and added to a solution of 2 g oxalic acid dihydrate in 75 ml of ether. The precipitated solid is collected by filtration and stirred in 20 ml of water. The insoluble salt is collected by filtration and dried to obtain 2.6 g of the oxalate salt of hexahydro-1'-benzyl-1-(3-trifluoromethylphenyl)spiro[3,4-oxazolo[3,4-a]pyridine-3,4'-piperidine]; mp 119°–120° C.

The alpha-(3-trifluoromethylphenyl)-2-piperidinemethanol used as a starting material in the above procedure can be prepared by utilizing the procedure described in Example 6 above for alpha-(2-methoxyphenyl)-2-piperidinemethanol.

EXAMPLE 9

Hexahydro-1-[3-(trifluoromethyl)phenyl[spiro[3H-oxazolo[3,4-a]pyridine-3,4'-piperidine] Oxalate Salt Utilizing the procedure described in Example 2 above, 2.5 g of hexahydro-1'-benzyl-1-(3-trifluoromethylphenyl)spiro[3,4-oxazolo[3,4-a]pyridine-3,4'-piperidine] is hydrogenated to obtain 1.5 g of hexahydro-1-[3-(trifluoromethyl)phenyl]spiro[3H-oxazolo[3,4-a]pyridine-3,4'piperidine] as an oil after evaporation of the organic layer. The oil, 1.5 g, is dissolved in 5 ml ether and added to a solution of 0.6 oxalic acid dihydrate in 5 ml of ether. The precipitated solid is collected by filtration and recrystallized from methanol-ethyl acetate to obtain the oxalate salt; mp 158°-160° C.

EXAMPLE 10

Hexahydro-1'-benzyl-1-(4-fluorophenyl)spiro[3H-oxazolo[3,4-a]pyridine-3,4'-piperidine]

A mixture of 6 g alpha-(4-fluorophenyl)-2-piperidinemethanol, 6 g of N-benzyl-4-piperidone and 0.2 g of p-toluenesulfonic acid in 200 ml of xylene is stirred under reflux for 48 hours in a vessel provided with a Dean-Stark water separator. The cooled mixture is filtered and evaporated in vacuo. The residue is applied to a silica gel column in ethyl acetate and chromatographed to obtain, hexahydro-1'-benzyl-1-(4-fluorophenyl)spiro[3H-oxazolo[3,4-a]pyridine-3,4'-piperidine]; mp 158°-159° C., after recrystallization from methanol.

EXAMPLE 11

Hexahydro-1-(4-fluorophenyl)spiro[3H-oxazolo[3,4-a]pyridine-3,4'-piperidine]

Utilizing the procedure described in Example 2 above, 4.8 g of hexahydro-1'-benzyl-1-(4-fluorophenyl)-spiro[3H-oxazolo[3,4-a]pyridine-3,4'-piperidine] is hydrogenated in the presence of a palladium on carbon catalyst to obtain hexahydro-1-(4-fluorophenyl)-spiro[3H-oxazolo[3,4-a]pyridine-3,4'-piperidien]; mp 112°-114° C., after recrystallization from methanol-water.

EXAMPLE 12

Hexahydro-1'-benzyl-1-(4-chlorophenyl)spiro[3H-oxazolo[3,4-a]pyridine-3,4'-piperidine]

A mixture of 17 g alpha-(4-chlorophenyl)-2-piperidinemethanol, 15 g of N-benzyl-4-piperidone, and 0.3 g of p-toluenesulfonic acid in 150 ml of xylene is stirred under reflux for 48 hours in a vessel provided with a Dean-Stark water separator. The cooled mixture is filtered and evaporated in vacuo. The residue is crystallized from methanol to provide the product, hexahydro-1'-benzyl-1-(4-chlorophenyl)spiro[3H-oxazolo[3,4-a]pyridine-3,4'-piperidine]; mp 134°-136° C.

EXAMPLE 13

Preparation of Hexahydro-1'-methyl-1-(4-chlorophenyl)spiro[3H-oxazolo[3,4-a]pyridine-3,4'-piperidine]

Utilizing the procedure described in Example 1 above, alpha-(4-chlorophenyl)-2-piperidinemethanol (10 g) is reacted with 1-methyl-4-piperidone (7 g) to yield hexahydro-1'-methyl-1-(4-chlorophenyl)spiro[3H-oxazolo[3,4-a]pyridine-3,4'-piperidine]; mp 122°-124° C., after chromatography over silica gel with ethyl acetate.

EXAMPLE 14

Hexahydro-1-(4-methoxyphenyl)spiro[3H-oxazolo[3,4-a]pyridine-3,4'-piperidine]

Utilizing the procedure described in Example 2 above, hexahydro-1'-benzyl-1-(4-methoxyphenyl)-spiro[3H-oxazolo[3,4-a]pyridine-3,4'-piperidine] is hydrogenated to obtain hexahydro-1-(4-methoxyphenyl)-spiro[3H-oxazolo[3,4-a]pyridine-3,4'-piperidine]; mp 128°-130° C., after recrystallization from methanol-water.

The hexahydro-1'-benzyl-1-(4-methoxyphenyl)-spiro[3H-oxazolo[3,4-a]pyridine-3,4'-piperidine] used as the starting material in the above procedure can be prepared by reacting alpha-(4-methoxyphenyl)-2-piperidinemethanol with N-benzyl-4-piperidone to obtain the starting material; mp 130°-133° C., after recrystallization from methanol.

EXAMPLE 15

Preparation of Hexahydro-1'-(cyclopropylmethyl)-1-phenylspiro[3H-oxazolo[3,4-a]pyridine-3,4'-piperidine]

A solution of 2.8 g of hexahydro-1'-(cyclopropylcarbonyl)-1-phenylspiro[3H-oxazolo[3,4-a]pyridine-3,4'-piperidine] in 25 ml of tetrahydrofuran is added dropwise to a stirred suspension of 0.6 g of lithium aluminum hydride in 50 ml of tetrahydrofuran and 70 ml of ether and the mixture is stirred under reflux for two hours. The reaction mixture is cooled and decomposed by the slow successive addition of 2 ml of water, 2 ml of 25% sodium hydroxide, and 5 ml of water. The mixture is filtered and the filtrate is evaporated in vacuo. The residue is crystallized from petroleum ether to obtain 1.4 g of solid, hexahydro-1'-(cyclopropylmethyl)-1-phenylspiro[3H-oxazolo[3,4-a]pyridine-3,4'-piperidine]; mp 108°-110° C.

The hexahydro-1'-(cyclopropylcarbonyl)-1-phenyl-spiro[3H-oxazolo[3,4-a]pyridine-3,4'-pipridine] used as the starting material in the above procedure can be prepared by the following procedure. Cyclopropanecarboxylic acid chloride, 2 g, is added dropwise to a stirred solution of 4 g of hexahydro-1-phenyl-spiro[3H-oxazolo[3,4-a]pyridine-3,4'-piperidine] and 2.8 ml of triethylamine in 100 ml of methylene dichloride at 50° C. the reaction mixture is allowed to stand at room temperature overnight and then stirred with 75 ml of water. The organic layer is separated, washed with a saturated aqueous solution of sodium bicarbonate, dried over magnesium sulfate and evaporated to dryness. The residual oil is crystallized from 30 ml of cyclohexane to obtain 4.2 g of hexahydro-1'-(cyclopropylcarbonyl)-1-phenylspiro[3H-oxazolo[3,4-a]pyridine-3,4'-piperidine]; mp 110°-114° C.

I claim:

1. A compound of the formula

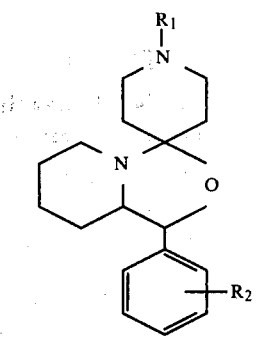

where $R_1$ is hydrogen, lower alkyl containing one to three carbon atoms, cycloalkyl lower alkyl containing four to seven carbon atoms, or benzyl; and $R_2$ is hydrogen, halogen, alkoxy containing one to three carbon atoms, or trifluoromethyl; and pharmaceutically acceptable acid addition salts thereof.

2. The compound of claim 1 having the same hexahydro-1-phenylspiro[3H-oxazolo[3,4-a]pyridine-3,4'-piperidine] and pharmaceutically acceptable acid addition salts thereof.

3. The compund of claim 1 having the name hexahydro-1'-methyl-1-phenylspiro[3H-oxazolo[3,4-a]pyridine-3,4'-piperidine] and pharmaceutically acceptable acid addition salts thereof.

4. The compound of claim 1 having the name hexahydro-1-(2-methoxyphenyl)spiro[3H-oxazolo[3,4-a]pyridine-3,4'-piperidine] and pharmaceutically acceptable acid addition salts thereof.

5. The compound of claim 1 having the same hexahydro-1-(3-fluorophenyl)spiro[3H-oxazolo[3,4-a]pyridine-3,4'piperidine] and pharmaceutically acceptable acid addition salts thereof.

6. The compound of claim 1 having the name hexahydro-1-[3-(trifluoromethyl)phenyl]spiro[3H-oxazolo[3,4-a]pyridine-3,4'-piperidine] and pharmaceutically acceptable acid addition salts thereof.

7. The compound of claim 1 having the name hexahydro-1-(4-fluorophenyl)spiro[3H-oxazolo[3,4-a]pyridine-3,4'-piperidine] and pharmaceutically acceptable acid addition salts thereof.

8. The compound of claim 1 having the name hexahydro-1'-methyl-1-(4-chlorophenyl)spiro[3H-oxazolo[3,4-a]pyridine-3,4'-piperidine] and pharmaceutically acceptable acid addition salts thereof.

9. The compound of claim 1 having the name hexahydro-1'-(cyclopropylmethyl)-1-phenylspiro[3H-oxazolo[3,4-a]pyridine-3,4'-piperidine] and pharmaceutically acceptable acid addition salts thereof.

10. A pharmaceutical composition for treating depression in mammals comprising an anti-depressive effective amount of a compound of the formula

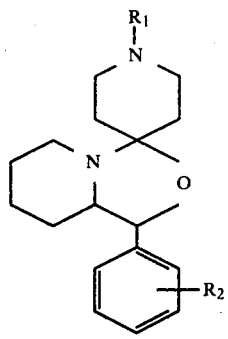

where $R_1$ is hydrogen, lower alkyl containing one to three carbon atoms, cycloalkyl lower alkyl containing four to seven carbon atoms, or benzyl; and $R_2$ is hydrogen, halogen, alkoxy containing one to three carbon atoms, trifluoromethyl; or a pharmaceutically acceptable salt thereof together with an inert pharmaceutical carrier.

11. A method of treating depression in mammals comprising the administration of an anti-depressive effective amount of a compound of the formula

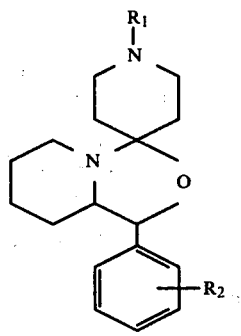

where $R_1$ is hydrogen, lower alkyl containing one to three carbon atoms, cycloalkyl lower alkyl containing four to seven carbon atoms, or benzyl; and $R_2$ is hydrogen, halogen, alkoxy containing one to three carbon atoms, trifluoromethyl; or of a pharmaceutically acceptable salt thereof.

* * * * *